United States Patent
Hayböck et al.

(10) Patent No.: US 11,493,517 B2
(45) Date of Patent: Nov. 8, 2022

(54) EUKARYOTIC TRANSLATION INITIATION FACTORS (EIFS) AS NOVEL BIOMARKERS IN HEAD AND NECK SQUAMOUS CELL CARCINOMA (HNSCC)

(71) Applicant: Otto-von-Guericke-Universität Magdeburg, Magdeburg (DE)

(72) Inventors: Johannes Hayböck, Innsbruck (AT); Anna Maria Cyran, Magdeburg (DE); Christoph Arens, Magdeburg (DE); Michael Naumann, Magdeburg (DE)

(73) Assignee: OTTO-VON-GUERICKE-UNIVERSITÄT MAGDEBURG, Magdeburg (DE)

( * ) Notice: Subject to any disclaimer, the term of this patent is extended or adjusted under 35 U.S.C. 154(b) by 108 days.

(21) Appl. No.: 16/840,744

(22) Filed: Apr. 6, 2020

(65) Prior Publication Data
US 2020/0333341 A1  Oct. 22, 2020

(51) Int. Cl.
*G01N 33/68* (2006.01)
*G01N 33/574* (2006.01)

(52) U.S. Cl.
CPC ......... *G01N 33/5748* (2013.01); *G01N 33/68* (2013.01)

(58) Field of Classification Search
CPC .................................................. G01N 33/5748
USPC ........................................................ 435/7.23
See application file for complete search history.

(56) References Cited

FOREIGN PATENT DOCUMENTS

WO   2015/175858 A1   11/2015

OTHER PUBLICATIONS

Gamper et al (BMC Genomics, 2009, 10(199): 1-17).*
European Search Report in EP 19170329, dated Oct. 24, 2019, 11 pages.
"Affymetrix GeneChip Human Genome U133 Array Set HG-U133A." GEO, Mar. 11, 2002.
Niknejad, et al. "Lovastatin-induced apoptosis is mediated by activating transcription factor 3 and enhanced in combination with salubrinal." International journal of cancer 134, No. 2 (2014): 268-279.
Ranganathan, et al. "Functional coupling of p38-induced up-regulation of BiP and activation of RNA-dependent protein kinase-like endoplasmic reticulum kinase to drug resistance of dormant carcinoma cells." Cancer research 66, No. 3 (2006): 1702-1711.
Ranganathan, et al. "Dual function of pancreatic endoplasmic reticulum kinase in tumor cell growth arrest and survival." Cancer research 6 8, No. 9 (2008): 3260-3268.
Spilka, et al. "Eukaryotic translation initiation factors in cancer development and progression." Cancer letters 340, No. 1 (2013): 9-21.

* cited by examiner

*Primary Examiner* — Sean E Aeder
(74) *Attorney, Agent, or Firm* — Kilpatrick Townsend & Stockton LLP

(57) ABSTRACT

The present invention relates to a method of diagnosing Head and Neck Squamous Cell Carcinoma (HNSCC) in an individual. In addition, the present invention relates to a method of providing a survival prognosis to an individual suffering from Head and Neck Squamous Cell Carcinoma (HNSCC). Moreover, the present invention relates to a kit for performing the above-mentioned methods.

7 Claims, 4 Drawing Sheets

|  | EIF2α |
|---|---|
| Neoplasm Clinical Primary Tumor Stage (T)* | 0.130 |
| Neoplasm Clinical Regional Lymph Node Stage (N)* | 0.087 |
| Neoplasm Clinical Distant Metastasis Stage (M)* | 0.111 |
| Neoplasm Clinical Group Stage* | 0.082 |
| Neoplasm Histologic Grade (G) | -0.010 |
| HPV-Status (p16) | -0.105 |
| Patient Smoking History Category | 0.091 |
| Patient Alcohol History Category | 0.062 |

* American Joint Committee on Cancer (AJCC)

EUKARYOTIC TRANSLATION INITIATION FACTORS (EIFS) AS NOVEL BIOMARKERS IN HEAD AND NECK SQUAMOUS CELL CARCINOMA (HNSCC)

The present invention relates to a method of diagnosing Head and Neck Squamous Cell Carcinoma (HNSCC) in an individual. In addition, the present invention relates to a method of providing a survival prognosis to an individual suffering from Head and Neck Squamous Cell Carcinoma (HNSCC). Moreover, the present invention relates to a kit for performing the above-mentioned methods.

BACKGROUND OF THE INVENTION

Head and Neck Squamous Cell Carcinoma (HNSCC) develops in the mucosa of the oral cavity, of the pharynx, larynx and paranasal sinuses. Every year over 68 0000 patients are diagnosed new with HNSCC worldwide, which represents 4.8% of all cancers. The mortality rate is estimated at 40-50%. In the early stages of the disease (stages 1 and II) the treatment consists mainly of surgical procedures or radiotherapy. For the locally advanced disease stages III and IV, multimodal treatment is recommended, including surgery with organ reconstruction followed by radiotherapy. For patients with increased risk of metastases, platinum-containing radiochemotherapy is indicated. Moreover, in non-resectable tumors in which surgical treatment is associated with a poor functional result, primary radiochemotherapy is preferred.

The upper aerodigestive tract is very complex relating to its anatomical structure and functionality. For this reason, HNSCC and its treatment is associated with diseases which influence the quality of life of survivors, such as dysphagia, loss of speech, aspiration of ingested foods leading to cachexia and cosmetic deficits. This underlines the need to provide therapies for the treatment of HNSCC.

Eukaryotic Initiation Factors (eIF) form a complex protein system controlling the first translation phase and the initiation phase. In the literature, a deregulation of various eIFs in human cancer types has been described. Furthermore, an increased protein synthesis is responsible for the development of tumors. Therefore, cancer cells are dependent on the increased protein production and may, therefore, be more susceptible to global translation inhibition than normal cells.

HNSCC is characterized by extraordinary intra- and inter-tumoral genetic heterogeneity. This is a problem in the context of radiation and chemotherapy. This heterogeneity may explain the different reactions of patients to HNSCC therapy and makes it difficult to develop targeted HNSCC therapies. One way to circumvent this, is the development of therapies against molecules which are deregulated in all cancer cells of the tumor, e.g. proteins of the translation machinery. Thus, there is an urgent need in the development of therapeutics being effective in HNSCC in view of its heterogeneity. In particular, it would be desirable to develop HSNCC therapeutics targeting the molecules of the translational machinery. There is also an urgent need to provide biomarkers allowing the reliable diagnosis of HNSCC in patients suspected of suffering from HNSCC and the reliable survival prognosis of patients suffering from HNSCC.

Recently, eIFs have been identified as potential markers and therapeutic targets of different tumor entities. EIF2S1/eIF2a, for example, plays an important role in translational initiation by transferring Met-tRNA to the 40S ribosomal subunit. Phosphorylation of the a subunit on Ser 51 deactivates eIF2. Although the exact mechanism remains unclear, it is likely that the phosphorylation of the a subgroup will lead to structural induced alterations in the β subunit, which in turn increase its affinity to eIF2S2/eIF2P. Its phosphorylation is described as a central regulator, which adapts the cells to different forms of stress and to the activity of the different kinases. Salubrinal acts by selectively inhibiting EIF2S1/eIF2a phosphatase and, thus, blocks EIF2S1/eIF2a in its inactive form. The inhibition of EIF2S1/eIF2a by Salubrinal in HNSCC has not been described yet.

The present inventors examined the mRNA expression data of 279 HNSCC patients and found that patients with high expression of all subunits of eIF2 and low expression of the eIF2AK1/HRI kinase showed a lower overall survival. Further, the present inventors found that an upregulation of all subunits of eIF2 and a downregulation of eIF2AK1/HRI compared to healthy controls is indicative for HNSCC. In particular, immunohistochemistry showed an overexpression of eIF2S1/eIF2a compared to non-tumorous tissue. Furthermore, the present inventors found that treatment with eIF2S1/eIF2a inhibitor Salubrinal leads to a reduction of cell viability in vitro and in 3D-cell culture.

SUMMARY OF THE INVENTION

In a first aspect, the present invention relates to a method of diagnosing Head and Neck Squamous Cell Carcinoma (HNSCC) in an individual (suspected of having HNSCC) comprising the step of:
determining the level of at least one eukaryotic Initiation Factor (eIF), wherein the at least one eIF is selected from the group consisting of eIF2S1, eIF2S2, eIF2S3, eIF2B1, eIF2B2, eIF2B3, eIF2B4, and eIF2B5, and/or the level of at least one eIF kinase, wherein the at least one eIF kinase is selected from the group consisting of eIF2AK1, eIF2AK2, eIF2AK3, and eIF2AK4, in a biological sample from an individual (suspected of having HNSCC).

In a second aspect, the present invention relates to a method of providing a survival prognosis to an individual suffering from Head and Neck Squamous Cell Carcinoma (HNSCC) comprising the step of:
determining the level of at least one eukaryotic Initiation Factor (eIF), wherein the at least one eIF is selected from the group consisting of eIF2S1, eIF2S2, eIF2S3, eIF2B1, eIF2B2, eIF2B3, eIF2B4, and eIF2B5, and/or the level of at least one eIF kinase, wherein the at least one eIF kinase is selected from the group consisting of eIF2AK1, eIF2AK2, eIF2AK3, and eIF2AK4, in a biological sample from an individual (suspected of having HNSCC).

In a third aspect, the present invention relates to the use of at least one eukaryotic Initiation Factor (eIF), wherein the at least one eIF is selected from the group consisting of eIF2S1, eIF2S2, eIF2S3, eIF2B1, eIF2B2, eIF2B3, eIF2B4, and eIF2B5, and/or at least one eIF kinase, wherein the at least one eIF kinase is selected from the group consisting of eIF2AK1, eIF2AK2, eIF2AK3, and eIF2AK4, for diagnosing Head and Neck Squamous Cell Carcinoma (HNSCC) in an individual (suspected of having HNSCC) or for providing a survival prognosis to an individual suffering from HNSCC.

In a fourth aspect, the present invention relates to a kit for diagnosing Head and Neck Squamous Cell Carcinoma (HNSCC) in an individual (suspected of having HNSCC) or for providing a survival prognosis to an individual suffering from HNSCC, wherein said kit comprises means for determining the level of at least one eukaryotic Initiation Factor (eIF), wherein the at least one eIF is selected from the group consisting of eIF2S1, eIF2S2, eIF2S3, eIF2B1, eIF2B2, eIF2B3, eIF2B4, and eIF2B5, and/or the level of at least one eIF kinase, wherein the at least one eIF kinase is selected from the group consisting of eIF2AK1, eIF2AK2, eIF2AK3, and eIF2AK4, in a biological sample from an individual.

In a fifth aspect, the present invention relates to an eukaryotic initiation factor (eIF) modulating compound for use in the treatment of HNSCC, wherein the at least one eIF is selected from the group consisting of eIF2S1, eIF2S2, eIF2S3, eIF2B1, eIF2B2, eIF2B3, eIF2B4, and eIF2B5.

In a sixth aspect, the present invention relates to a combination of an eIF modulating compound and a drug different from an eIF modulating compound for use in the treatment of HNSCC, wherein the at least one eIF is selected from the group consisting of eIF2S1, eIF2S2, eIF2S3, eIF2B1, eIF2B2, eIF2B3, eIF2B4, and eIF2B5.

In a seventh aspect, the present invention relates to a pharmaceutical composition comprising the eIF modulating compound or the combination disclosed herein and a pharmaceutical acceptable carrier for use in the treatment of HNSCC.

This summary of the invention does not necessarily describe all features of the present invention. Other embodiments will become apparent from a review of the ensuing detailed description.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention. In the event of a conflict between the definitions or teachings of such incorporated references and definitions or teachings recited in the present specification, the text of the present specification takes precedence.

The term "comprise" or variations such as "comprises" or "comprising" according to the present invention means the inclusion of a stated integer or group of integers but not the exclusion of any other integer or group of integers. The term "consisting essentially of" according to the present invention means the inclusion of a stated integer or group of integers, while excluding modifications or other integers which would materially affect or alter the stated integer. The term "consisting of" or variations such as "consists of" according to the present invention means the inclusion of a stated integer or group of integers and the exclusion of any other integer or group of integers.

The terms "a" and "an" and "the" and similar reference used in the context of describing the invention (especially in the context of the claims) are to be construed to cover both the singular and the plural, unless otherwise indicated herein or clearly contradicted by context.

The term "Head and Neck Squamous Cell Carcinoma (HNSCC)", as used herein, refers to malignant neoplasms that arise in the head and neck region which comprises nasal cavity, paranasal sinuses, oral cavity, salivary glands, pharynx, and larynx. HNSCC is the 6th most common cancers worldwide and 3rd most common cancers in developing world. Risk factors include tobacco consumption (chewing or smoking), alcohol consumption, Epstein-Barr virus (EBV) infection, human papilloma virus (HPV; esp. HPV 16 and 18) infection, *betel* nut chewing, wood dust exposures, consumption of certain salted fish and others. EBV infection has been specifically associated with nasopharyngeal cancer. Reverse smoking was considered as a risk factor for oral cancer. Cis-retinoic acid (i.e. supplements of retinoic acid) intake may increase the risk of HNSCC in smokers. Low consumption of fruits and vegetables was associated with higher incidence of HNSCC. HNSCC is preferably selected from the group consisting of Neoplasm Clinical Primary Tumor Stage (T), Neoplasm Clinical Regional Lymph Node Stage (N), and Neoplasm.

The term "diagnosis", as used herein, refers to the process of determining a possible disease or disorder and, therefore, is a process attempting to define the (clinical) condition of an individual. The determination of the eIF level and/or eIF kinase level correlates with the (clinical) condition of an individual.

The term "diagnosing HNSCC", as used herein, means determining whether an individual shows signs of or suffers from HNSCC. Preferably, the diagnosis of HNSCC comprises/encompasses (i) determining the occurrence/presence of HNSCC, (ii) monitoring the course of HNSCC, (iii) staging HNSCC, (iv) measuring the response of an individual with HNSCC to therapeutic intervention, and/or (v) segmentation of an individual suffering from HNSCC.

The term "(survival) prognosis", as used herein, refers to the prediction of the likelihood/probability of death of an individual suffering from HNSCC. The term "providing a (survival) prognosis to an individual suffering from HNSCC", as used herein, refers to the prediction of the likelihood/probability of death of an individual suffering from HNSCC. In particular, the term "providing a (survival) prognosis to an individual suffering from HNSCC", as used herein, means determining whether an individual has a good prognosis (low probability of death) or a poor prognosis (high probability of death) with respect to HNSCC.

An individual suffering from HNSCC may be considered to have a "good prognosis (low probability of death)" where, for example, the survival rate associated with HNSCC is greater compared to the survival rate of (control) subjects suffering from the same disease. Preferably, an individual suffering from HNSCC may be considered to have a "good prognosis" where, for example, the survival rate associated with HNSCC is greater compared to the survival rate of (control) subjects suffering from the same disease and showing another (expression) level of one or more of the prognostic biomarkers of the present invention. The prognostic biomarkers of the present invention are eukaryotic Initiation Factors (eIFs), wherein the eIFs are selected from the group consisting of eIF2S1, eIF2S2, eIF2S3, eIF2B1, eIF2B2, eIF2B3, eIF2B4, and eIF2B5, and/or eIF kinases, wherein the eIF kinases are selected from the group consisting of eIF2AK1, eIF2AK2, eIF2AK3, and eIF2AK4.

In certain embodiments, a "good prognosis" indicates at least an increased expected survival time. A "good prognosis" indicates a greater than 1%, preferably greater than 10%, more preferably greater than 20%, more preferably greater than 30%, more preferably greater than 40%, more preferably greater than 50%, more preferably greater than 60%, more preferably greater than 70%, more preferably greater than 80%, more preferably greater than 90%, chance that the individual will survive at least to a specified time point (such as at least 1, 2, 3, 4, 5, 6 or 12 month(s) or even 1, 2, 3, 4, or 5 year(s)) or a specific time period (such as at least a 1-year, 2-year, 3-year, 4-year, or 5-year period).

An individual suffering from a HNSCC may be considered to have a "poor prognosis (high probability of death)" where, for example, the survival rate associated with HNSCC is lower compared to the survival rate of (control) subjects suffering from the same disease. Preferably, an individual suffering from HNSCC may be considered to have a "poor prognosis" where, for example, the survival rate associated with HNSCC is lower compared to the survival rate of (control) subjects suffering from the same disease and showing another (expression) level of one or more of the prognostic markers of the present invention. The prognostic biomarkers of the present invention are eukaryotic Initiation Factors (eIFs), wherein the eIFs are selected from the group consisting of eIF2S1, eIF2S2, eIF2S3, eIF2B1, eIF2B2, eIF2B3, eIF2B4, and eIF2B5, and/or eIF kinases, wherein the eIF kinases are selected from the group consisting of eIF2AK1, eIF2AK2, eIF2AK3, and eIF2AK4.

In certain embodiments, a "poor prognosis" indicates at least a decreased expected survival time. A "poor prognosis" indicates a lower than 1%, preferably lower than 10%, more preferably lower than 20%, more preferably lower than 30%, more preferably lower than 40%, more preferably lower than 50%, more preferably lower than 60%, more preferably lower than 70%, more preferably lower than 80%, more preferably lower than 90%, chance that the individual will survive at least to a specified time point (such as at least 1, 2, 3, 4, 5, 6 or 12 month(s) or even 1, 2, 3, 4, or 5 year(s)) or a specific time period (such as at least a 1-year, 2-year, 3-year, 4-year, or 5-year period).

The prognostic method can be used clinically to determine the survival prognosis/survival probability of an individual suffering from HNSCC. In particular, the method of providing a survival prognosis to an individual suffering from HNSCC is a valuable tool in predicting whether overall (or long-term) survival of the individual, e.g. following therapy, is likely. The prognostic method can also be used clinically to make treatment decisions by choosing the most appropriate treatment modalities for any particular individual suffering from HNSCC. In particular, the method of providing a survival prognosis to an individual suffering from HNSCC is a valuable tool in predicting if an individual is likely to respond favorably to a treatment regimen, such as drug therapy and/or surgical intervention.

The term "overall survival", as used herein, refers to an individual's survival suffering from HNSCC for at least 1 year, 2 years, at least 5 years, at least 8 years, or at least 10 years, e.g. following treatment such as drug therapy, radiotherapy, chemotherapy, and/or surgical intervention.

The term "individual", as used herein, refers to any subject for whom it is desired to know whether she or he suffers from HNSCC. In particular, the term "individual", as used herein, refers to a subject suspected to be affected by HNSCC. The individual may be diagnosed to be affected by HNSCC, i.e. diseased, or may be diagnosed to be not affected by HNSCC, i.e. healthy. The term "individual", as used herein, also refers to a subject which is affected by HNSCC, i.e. diseased. The individual may be retested for HNSCC in order to determine the individual's survival prognosis. The individual known to suffer HNSCC, e.g. from Neoplasm Clinical Primary Tumor Stage (T), may also be retested for HNSCC and may be diagnosed as having developed an advanced form of HNSCC, e.g. Neoplasm Clinical Regional Lymph Node Stage (N) or Neoplasm Clinical Distant Metastasis Stage (M).

It should be noted that an individual that is diagnosed as being healthy, i.e. not suffering from HNSCC, may possibly suffer from another disease or condition not tested/known.

The individual may be any mammal, including both a human and another mammal, e.g. an animal such as a rabbit, mouse, rat, or monkey. Human individuals are particularly preferred.

The term "(control) subject", as used herein, refers to an individual known to be not affected by HNSCC (negative control), i.e. healthy, or known to be affected by HNSCC, i.e. diseased. The (control) subject may suffer from Neoplasm Clinical Primary Tumor Stage (T), Neoplasm Clinical Regional Lymph Node Stage (N), or Neoplasm Clinical Distant Metastasis Stage (M).

The (control) subject may be any mammal, including both a human and another mammal, e.g. an animal such as a rabbit, mouse, rat, or monkey. Human (control) patients are particularly preferred. It should be noted that a subject which is known to be healthy, i.e. not suffering from HNSCC, may possibly suffer from another disease or condition not tested/known.

The term "eukaryotic Initiation Factor (eIF)", as used herein, refers to molecules which are involved in the initiation phase of eukaryotic translation. These factors help to stabilize the formation of the functional ribosome around the start codon and also provide regulatory mechanisms in translation initiation. The term "eukaryotic Initiation Factor (eIF)", as used herein, covers eIF RNA transcripts (RNA transcript variants) such as mRNAs including splice variants of these transcripts and eIF proteins encoded thereby. Thus, the level of the eIFs may be determined by measuring mRNA or protein levels. The term "eukaryotic Initiation Factor (eIF)", as used herein, also covers eIF isoforms. These eIF isoforms are members of a set of highly similar molecules, in particular proteins, that perform the same or similar biological role. Described herein are the eIFs: eIF2S1/EIF2S1/eIF2α/eIF2alpha, eIF2S2/EIF2S2/eIF2β/eIF2beta, eIF2S3/EIF2S3/eIF2γ/eIF2gamma, eIF2B1/EIF2B1/eIF2Bα/eIF2Balpha, eIF2B2/EIF2B2/eIF2Bβ/eIF2Bbeta, eIF2B3/EIF2B3/eIF2Bγ/eIF2Bgamma, eIF2B4/EIF2B4/eIF2Bδ/eIF2Bdelta, and eIF2B5/EIF2B5/eIF2Bε/eIF2Bepsilon.

The term "kinase", as used herein, refers to an enzyme that catalyses the transfer of phosphate groups from high-energy, phosphate-donating molecules to specific substrates. This process is known as phosphorylation, where the substrate gains a phosphate group and the high-energy ATP molecule donates a phosphate group.

The term "eukaryotic Initiation Factor (eIF) kinase", as used herein, refers to kinases that phosphorylate eIFs. Described herein are the eIF kinases: eIF2AK1/HRI, eIF2AK2/PKR, eIF2AK3/PEK, and eIF2AK4/GCN2.

The term "biological sample", as used herein, refers to any biological sample from an individual or (control) subject comprising at least one of the eIFs and/or eIF kinases mentioned herein. The biological sample may be a body fluid sample, e.g. a blood sample or urine sample, or a tissue sample. Biological samples may be mixed or pooled, e.g. a sample may be a mixture of a blood sample and a urine sample. Said biological samples may be provided by removing a body fluid from an individual or (control) subject, but may also be provided by using a previously isolated sample. For example, a blood sample may be taken from an individual or (control) subject by conventional blood collection techniques. The biological sample, e.g. urine sample or blood sample, may be obtained from an individual or (control) subject prior to the initiation of a therapeutic treatment, during the therapeutic treatment, and/or after the therapeutic treatment. If the sample, in particular the biological sample, is obtained from at least one (control) subject, e.g. from at least 1, 2, 3, 4, 5, 6, 7, 8, 9, 10, 20, 30, 40, 50, 60, 70, 80, 90, 100, 150, 200, 250, 300, 400, 500, or 1.000 (control) (control) subject(s), it is designated as a "reference biological sample". Preferably, the reference biological sample is from the same source than the biological sample of the individual to be tested, e.g. both are blood samples or urine samples. It is further preferred that both are from the same species, e.g. from a human. It is also (alternatively or additionally) preferred that the measurements of the reference biological sample and the biological sample of the individual to be tested are identical, e.g. both have an identical volume. It is particularly preferred that the reference biological sample and the biological sample are from individuals/(control) patients of the same sex and similar age, e.g. no more than 2 years apart from each other.

The term "body fluid sample", as used herein, refers to any liquid sample derived from the body of an individual or (control) subject containing at least one of the eIFs and/or eIF kinases mentioned herein. Said body fluid sample may be a urine sample, blood sample, sputum sample, breast milk sample, cerebrospinal fluid (CSF) sample, cerumen (earwax) sample, gastric juice sample, mucus sample, lymph sample, endolymph fluid sample, perilymph fluid sample, peritoneal fluid sample, pleural fluid sample, saliva sample, sebum (skin oil) sample, semen sample, sweat sample, tears sample, cheek swab, vaginal secretion sample, liquid biopsy, or vomit sample including components or fractions thereof. The term "body fluid sample" also encompasses body fluid fractions, e.g. blood fractions, urine fractions or sputum fractions. Body fluid samples may be mixed or pooled. Thus, a body fluid sample may be a mixture of a blood and a urine sample or a mixture of a blood and cerebrospinal fluid sample. Said body fluid sample may be provided by removing a body liquid from an individual or (control) patient, but may also be provided by using previously isolated body fluid sample material. The body fluid sample allows for a non-invasive analysis of an individual. It is further preferred that the body fluid sample has a volume of between 0.01 and 20 ml, more preferably of between 0.1 and 10 ml, even more preferably of between 0.5 and 8 ml, and most preferably of between 1 and 5 ml.

The term "blood sample", as used herein, encompasses a whole blood sample or a blood fraction sample such as a blood serum or blood plasma sample. It is preferred that the blood serum or plasma sample has a volume of between 0.01 and 20 ml, more preferably of between 0.1 and 10 ml, even more preferably of between 0.5 and 8 ml and most preferably of between 1 and 5 ml.

The term "level", as used herein, refers to an amount (measured for example in grams, mole, or counts such as ion or fluorescence counts) or concentration (e.g. absolute or relative concentration) of the eIFs and/or eIF kinases described herein. The term "level", as used herein, also comprises scaled, normalized, or scaled and normalized amounts or values. Preferably, the level is an expression level. The level may also be a reference level. The reference level may be an average reference level. It may be determined by measuring reference levels and calculating the "average" value (e.g. mean, median or modal value) thereof.

In the context of the present invention, the term "kit of parts (in short: kit)" is understood to be any combination of at least some of the components identified herein, which are combined, coexisting spatially, to a functional unit, and which can contain further components. Said kit may allow point-of-care testing (POCT).

The term "point-of-care testing (POCT)", as used herein, refers to a medical diagnostic testing at or near the point of care that is the time and place of individual care. This contrasts with the historical pattern in which testing was wholly or mostly confined to the medical laboratory, which entailed sending off specimens away from the point of care and then waiting hours or days to learn the results, during which time care must continue without the desired information. Point-of-care tests are simple medical tests that can be performed at the bedside. The driving notion behind POCT is to bring the test conveniently and immediately to the individual to be tested. This increases the likelihood that the individual, physician, and care team will receive the results quicker, which allows for immediate clinical management decisions to be made. POCT is often accomplished through the use of transportable, portable, and handheld instruments and test kits. Small bench analyzers or fixed equipment can also be used when a handheld device is not available—the goal is to collect the specimen and obtain the results in a very short period of time at or near the location of the individual so that the treatment plan can be adjusted as necessary before the individual leaves the hospital.

The term "treatment", in particular "therapeutic treatment", as used herein, refers to any therapy which improves the health status and/or prolongs (increases) the lifespan of an individual suffering from a disease or condition, in particular a tumor. Said therapy may eliminate the disease or condition in an individual, arrest or slow the development of a disease in an individual, inhibit or slow the development of a disease in an individual, decrease the frequency or severity of symptoms in an individual, and/or decrease the recurrence in an individual who currently has or who previously has had a disease. The treatment of HNSCC described herein includes, but is not limited to, administration of a drug, surgery, chemotherapy, and/or radiotherapy.

The term "eukaryotic Initiation Factor (eIF) modulating compound", as used herein, refers to a molecule which is able to influence the level of eIF within the cell. The presence of the eIF modulating compound may increase the eIF level or decrease the eIF level within the cell. The eIF modulating compound may be a eIF binding/inhibiting molecule or a eIF molecule. The administration of a eIF binding/inhibiting molecule may reduce the level of the eIF within the cell and/or block its function within the cell. The administration of a eIF molecule may increase the level of the eIF within the cell and/or improves its function within the cell. In the context of the present invention, the eIF modulating compound is a eIF2S1, eIF2S2, eIF2S3, eIF2B1, eIF2B2, eIF2B3, eIF2B4, and/or eIF2B5 modulating compound.

The term "eIF binding/inhibiting molecule", as used herein, refers to a compound which is able to bind to, hybridize with, or inhibit an eIF. Preferably, the eIF binding/ inhibiting molecule is selected from the group consisting of an anti-RNA, a small interfering RNA (siRNA), a short hairpin RNA (shRNA), a polypeptide or peptide, preferably comprising at least one eIF binding site, and an antibody or an antibody fragment thereof, preferably comprising at least one eIF binding site.

Said eIF binding/inhibiting molecule can decrease the expression of the eIF or block the eIF. The eIF activity can be inhibited or significantly reduced by using said eIF binding/inhibiting molecule. Due to its binding, the biochemical and biological function of the eIF is inhibited or at least partially inhibited. Due to its inhibition, the eIF is blocked. In the context of the present invention, the eIF binding/inhibiting molecule is a eIF2S1, eIF2S2, eIF2S3, eIF2B1, eIF2B2, eIF2B3, eIF2B4, and/or eIF2B5 binding/inhibiting molecule.

The term "anti-RNA", as used herein, refer to molecules that have many uses in cellular mechanics. Anti-RNAs are synthetically designed molecules which are used to neutralize RNA function in cells for desired responses.

RNA blocking/inhibition can also be achieved by using RNA interference (RNAi) technology. RNA interference uses typically small interfering RNAs (siRNAs) and/or short hairpin RNAs (shRNAs). The administration of such molecules (e.g. siRNAs, shRNAs) leads to a decrease of the level of the eIF within the cell.

The term "siRNA", as used herein, refers to typically double-stranded RNA molecules (dsRNA) that mediate the targeted cleavage of a RNA transcript via a RNA-induced silencing complex (RISC) pathway. siRNA molecules interfere with the expression of specific genes with complementary nucleotide sequences by degrading mRNA after transcription.

The terms "short hairpin RNA (shRNA)" or "small hairpin RNA (shRNA)", as used herein, refer to an artificial RNA molecule with a tight hairpin turn that can be used to silence target gene expression via RNA interference (RNAi). In particular, the shRNAs comprise a hairpin structure (also called stem loop). In a preferred embodiment, shRNAs comprise a short antisense strand, followed by a nucleotide loop of about 5 to about 9 nucleotides, and the analogous sense strand. Alternatively, the sense strand may precede the nucleotide loop structure and the antisense strand may follow.

The terms "antibody", "immunoglobulin", "Ig" and "Ig molecule" are used interchangeably herein. They refer to Y-shaped proteins that are produced by the immune system to help stop intruders from harming the body. When an intruder enters the body, the immune system springs into action. These invaders, which are called antigens, can be viruses, bacteria, or other chemicals. When an antigen is found in the body, the immune system will create antibodies to mark the antigen for the body to destroy. The terms are used in their broadest sense and include monoclonal antibodies (including full length monoclonal antibodies), polyclonal antibodies, single chain antibodies, and multispecific antibodies (e.g. bispecific antibodies). The term "antibody fragment", as used herein, refers to a polypeptide that includes at least one immunoglobulin variable domain or immunoglobulin variable domain sequence and which specifically binds a specific antigen. An antibody fragment can comprise an antibody or a polypeptide comprising an antigen-binding domain of an antibody. An antibody fragment can comprise a monoclonal antibody or a polypeptide comprising an antigen-binding domain of a monoclonal antibody. For example, an antibody can include a heavy (H) chain variable region and a light (L) chain variable region. An antibody may include two heavy (H) chain variable regions and two light (L) chain variable regions. The term "antibody fragment" encompasses antigen-binding fragments of antibodies such as single chain antibodies, Fab fragments, F(ab')$_2$, Fv fragments and scFv. An antibody can have the structural features of IgA, IgG, IgE, IgD, IgM (as well as subtypes and combinations thereof). Antibodies can be from any source, including mouse, rabbit, pig, rat, and primate (human and non-human primate), whereby the antibodies have to be humanized before administered to a patient. Methods to humanize antibodies are well known in the art. The antibody or a fragment thereof may also be used to bind to/block/neutralize an eIF.

The administration of such an eIF binding/inhibiting molecule leads to a decrease in expression of the eIF and/or function of the eIF. In some embodiments, eIF expression is decreased and/or eIF blocking is achieved for an extended duration, e.g., at least one week, two weeks, three weeks, or four weeks or longer. For example, in certain instances, eIF expression and/or eIF function is suppressed by at least about 5%, preferably at least 10%, more preferably at least 15%, more preferably at least 20%, more preferably at least 25%, more preferably at least 30%, more preferably at least 40%, more preferably at least 50%, more preferably at least 60%, more preferably at least 70%, more preferably at least 80%, more preferably at least 90%, by administration of the eIF binding/inhibiting molecule described herein.

In an alternative approach, to increase the level of a eIF within a cell, the eIF modulating compound is a "eIF molecule", e.g. a nucleic acid molecule encoding the eIF. The administration of such a nucleic acid molecule is advantageous because it can be used to express the eIF within the body. The nucleic acid molecule is preferably a DNA or RNA molecule, wherein the DNA molecule is preferably comprised in an expression vector, preferably an expression plasmid. The expression vector preferably comprises a promoter. Promoters which can be used for this purpose include a cytomegalovirus (CMV) promoter, thymidine kinase (TK) promoter of herpes simplex virus (HSV), SV40 promoter, etc.

The administration of such an eIF molecule leads to an increase in expression of the eIF or increase of the level of the eIF within the cell. In some embodiments, the eIF expression is increased or eIF level is increased for an extended duration, e.g., at least one week, two weeks, three weeks, or four weeks or longer. For example, in certain instances, the eIF expression or eIF level is increased by at least about 5%, preferably at least 10%, more preferably at least 15%, more preferably at least 20%, more preferably at least 25%, more preferably at least 30%, more preferably at least 40%, more preferably at least 50%, more preferably at least 60%, more preferably at least 70%, more preferably at least 80%, more preferably at least 90%, by administration of the eIF molecule described herein.

In a specific embodiment of the present invention, the eIF modulating compound is Salubrinal. In particular, Salubrinal blocks/inhibits/affects the eIFs, preferably eIF2S1. This effect can be achieved directly or indirectly.

It is preferred that the eIF modulating compound is suitable to be administered topically, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctivally, intravesicularly, mucosally, intrapericardially, intraumbilically, orally, by inhalation, by injection, by infusion, by continuous infusion, by localized perfusion bathing target cells directly, via a catheter, or via a lavage. It is also preferred that the eIF modulating compound is suitable to be administered by providing a delivery system selected from the group consisting of an expression construct, preferably a vector, more preferably a viral vector, even more preferably an adenovirus, an adeno-associated virus, a retrovirus, or a lentivirus vector, a liposome, a polymer-mediated delivery system, a conjugate delivery system, an exosome, a microsponge, and a nanoparticle, preferably a gold particle.

The eIF modulating compound may be administered in the form of any suitable pharmaceutical composition. Said pharmaceutical composition may further comprise pharmaceutical acceptable carriers, diluents, and/or excipients.

The term "systemic administration", a used herein, refers to the administration of the eIF modulating compound such that said compound becomes widely distributed in the body of a patient in significant amounts and develops a biological effect. Typical systemic routes of administration include administration by introducing the eIF modulating compound directly into the vascular system or oral, pulmonary, or intramuscular administration wherein the eIF modulating compound enters the vascular system and is carried to one or more desired site(s) of action via the blood. The systemic administration may be by parenteral administration. The term "parenteral administration", as used herein, refers to the administration of the eIF modulating compound such that said compound does not pass the intestine. The term "parenteral administration" includes intravenous administration, subcutaneous administration, intradermal administration, or intraarterial administration, but is not limited thereto.

The pharmaceutical composition according to the present invention is generally applied in a "pharmaceutically effective amount". The term "pharmaceutically effective amount", as used herein, refers to the amount which achieves a desired reaction or a desired effect alone or together with further doses. In case of the treatment of a particular disease, the desired reaction preferably relates to an inhibition of the course of the disease. This comprises slowing down the progress of the disease and, in particular, interrupting or reversing the progress of the disease. The desired reaction in a treatment of a disease may also be a delay of the onset or a prevention of the onset of the disease. An effective amount of the compounds or compositions described herein will depend on the condition to be treated, the severeness of the disease, the individual parameters of the patient, including age, physiological condition, size, and weight, the duration of treatment, the type of an accompanying therapy (if present), the specific route of administration, and similar factors. Accordingly, the doses of the compounds or compositions described herein may depend on various of such parameters. In case that a reaction in the patient/subject is insufficient with an initial dose, higher doses (or effectively higher doses achieved by a different, more localized route of administration) may be used.

As mentioned above, the pharmaceutical composition of the present invention may further comprise pharmaceutical acceptable carriers, diluents, and/or excipients.

The term "excipient", as used herein, is intended to indicate all substances in a pharmaceutical composition which are not active ingredients such as binders, lubricants, thickeners, surface active agents, preservatives, emulsifiers, buffers, flavoring agents, or colorants.

The term "diluent", as used herein, relates to a diluting and/or thinning agent. Moreover, the term "diluent" includes a solution, suspension (e.g. liquid or solid suspension) and/or media.

The term "carrier", as used herein, relates to one or more compatible solid or liquid fillers, which are suitable for an administration, e.g. to a human. The term "carrier" relates to a natural or synthetic organic or inorganic component which is combined with an active component in order to facilitate the application of the active component. Preferably, carrier components are sterile liquids such as water or oils, including those which are derived from mineral oil, animals, or plants, such as peanut oil, soy bean oil, sesame oil, sunflower oil, etc. Salt solutions and aqueous dextrose and glycerin solutions may also be used as aqueous carrier compounds.

Pharmaceutically acceptable carriers or diluents for therapeutic use are well known in the pharmaceutical art, and are described, for example, in Remington's Pharmaceutical Sciences, Mack Publishing Co. (A. R Gennaro edit. 1985). Examples of suitable carriers include, for example, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Examples of suitable diluents include ethanol, glycerol, and water.

Pharmaceutical carriers, diluents, and/or excipients can be selected with regard to the intended route of administration and standard pharmaceutical practice. The pharmaceutical compositions of the present invention may comprise as, or in addition to, the carrier(s), excipient(s) or diluent(s) any suitable binder(s), lubricant(s), suspending agent(s), coating agent(s), and/or solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose, and polyethylene glycol. Examples of suitable lubricants include sodium oleate, sodium stearate, magnesium stearate, sodium benzoate, sodium acetate, sodium chloride, and the like. Preservatives, stabilizers, dyes, and even flavoring agents may be provided in the pharmaceutical composition. Examples of preservatives include sodium benzoate, sorbic acid, and esters of p-hydroxybenzoic acid. Antioxidants and suspending agents may be also used.

Embodiments of the Invention

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous, unless clearly indicated to the contrary.

As mentioned above, HNSCC is characterized by extraordinary intra- and inter-tumoral genetic heterogeneity. This is a problem in the context of radiation and chemotherapy. This heterogeneity may explain the different reactions of patients to HNSCC therapy and makes it difficult to develop targeted HNSCC therapies. One way to circumvent this, is the development of therapies against molecules which are deregulated in all cancer cells of the tumor, e.g. proteins of the translation machinery. Thus, there is an urgent need in the development of therapeutics being effective in HNSCC in view of its heterogeneity. In particular, it would be desirable to develop HSNCC therapeutics targeting the molecules of the translational machinery. There is also an urgent need to provide biomarkers allowing the reliable diagnosis of HNSCC in patients suspected of suffering from HNSCC and the reliable survival prognosis of patients suffering from HNSCC.

The present inventors examined the mRNA expression data of 279 HNSCC patients and found that patients with high expression of all subunits of eIF2 and low expression of the eIF2AK1/HRI kinase showed a lower overall survival. Further, the present inventors found that an upregulation of all subunits of eIF2 and a downregulation of eIF2AK1/HRI compared to healthy controls is indicative for HNSCC. In particular, immunohistochemistry showed an overexpression of eIF2S1/eIF2α compared to non-tumorous tissue. Furthermore, the present inventors found that treatment with eIF2S1/eIF2α inhibitor Salubrinal leads to a reduction of cell viability in vitro and in 3D-cell culture.

Thus, in a first aspect, the present invention relates to a method of diagnosing Head and Neck Squamous Cell Carcinoma (HNSCC) in an individual (suspected of having HNSCC) comprising the step of:
determining the level of at least one eukaryotic Initiation Factor (eIF), wherein the at least one eIF is selected from the group consisting of eIF2S1, eIF2S2, eIF2S3, eIF2B1, eIF2B2, eIF2B3, eIF2B4, and eIF2B5, and/or the level of at least one eIF kinase, wherein the at least one eIF kinase is selected from the group consisting of eIF2AK1, eIF2AK2, eIF2AK3, and eIF2AK4, in a biological sample from an individual (suspected of having HNSCC).

Preferably, the method is carried out in vitro.

In particular, said individual is suspected of suffering from HNSCC.

For example, the level(s) of at least 1, 2, 3, 4, 5, 6, 7, or 8 eIF(s) and/or at least 1, 2, 3, or 4 eIF kinase(s) is (are) determined. Preferably, the level of eIF2S1 and/or the level of eIF2AK1 is (are) determined.

In one embodiment, the level of the at least one eIF is compared to a reference level of said at least one eIF.

The above comparison allows to diagnose HNSCC in an individual, in particular in an individual suspected of having HNSCC. The individual may be diagnosed as suffering from HNSCC, i.e. being diseased, or as not suffering from HNSCC, i.e. being healthy.

Preferably, the reference level is the level determined by measuring at least one reference biological sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference biological sample(s), from at least one healthy subject, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 healthy subject(s).

It is practicable to take one reference biological sample per individual for analysis. If additional reference biological samples are required, e.g. to determine the reference level in different reference biological samples, the same individual may be (re)tested. Said reference level may be an average reference level. It may be determined by measuring reference levels and calculating the "average" value (e.g. mean, median or modal value) thereof.

More preferably, the level of the at least one eIF above the reference level indicates that the individual suffers from HNSCC.

Even more preferably, the level of the at least one eIF is at least 0.6-fold or 0.7-fold, more preferably at least 0.8-fold or 0.9-fold, even more preferably at least 1.2-fold or 1.5-fold, and most preferably at least 2.0-fold or 3.0-fold above the reference level. For example, the level of the at least one eIF is at least 0.6-fold, at least 0.7-fold, at least 0.8-fold, at least 0.9-fold, at least 1.0-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, or at least 3.0-fold above the reference level.

In one another (additional or alternative) embodiment, the level of the at least one eIF kinase is compared to a reference level of said at least one eIF kinase.

The above comparison allows to diagnose HNSCC in an individual, in particular in an individual suspected of having HNSCC. The individual may be diagnosed as suffering from HNSCC, i.e. being diseased, or as not suffering from HNSCC, i.e. being healthy.

Preferably, the reference level is the level determined by measuring at least one reference biological sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference biological sample(s), from at least one healthy subject, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 healthy subject(s).

More preferably, the level of the at least one eIF kinase below the reference level indicates that the individual suffers from HNSCC.

Even more preferably, the level of the at least one eIF kinase is at least 0.6-fold or 0.7-fold, more preferably at least 0.8-fold or 0.9-fold, even more preferably at least 1.2-fold or 1.5-fold, and most preferably at least 2.0-fold or 3.0-fold below the reference level. For example, the level of the at least one eIF kinase is at least 0.6-fold, at least 0.7-fold, at least 0.8-fold, at least 0.9-fold, at least 1.0-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, or at least 3.0-fold below the reference level.

In a second aspect, the present invention relates to a method of providing a survival prognosis to an individual suffering from Head and Neck Squamous Cell Carcinoma (HNSCC) comprising the step of:
determining the level of at least one eukaryotic Initiation Factor (eIF), wherein the at least one eIF is selected from the group consisting of eIF2S1, eIF2S2, eIF2S3, eIF2B1, eIF2B2, eIF2B3, eIF2B4, and eIF2B5, and/or the level of at least one eIF kinase, wherein the at least one eIF kinase is selected from the group consisting of eIF2AK1, eIF2AK2, eIF2AK3, and eIF2AK4, in a biological sample from an individual (suspected of having HNSCC).

Preferably, the method is carried out in vitro.

For example, the level(s) of at least 1, 2, 3, 4, 5, 6, 7, or 8 eIF(s) and/or at least 1, 2, 3, or 4 eIF kinase(s) is (are) determined. Preferably, the level of eIF2S1 and/or the level of eIF2AK1 is (are) determined.

In particular, the method of providing a survival prognosis to an individual suffering from HNSCC is carried out at the time of HNSCC diagnosis, immediately after HNSCC diagnosis, e.g. within 1 week, 2 week, 3 weeks, or 1 month after HNSCC diagnosis, or within a time period after HNSCC diagnosis, e.g. within a time period of no more than 1 week, 2 weeks, 3 weeks, 1 month, 2 months, 3 months, 4 months, 5 months, 6 months, 1 year, 2 years, 3 years, or 4 years after HNSCC diagnosis. The method of providing a survival prognosis to an individual suffering from HNSCC may also be repeated several times during the disease/illness period in order to determine, whether the survival prognosis has changed, e.g. from a good survival prognosis to a low survival prognosis or from a low survival prognosis to a good survival prognosis.

It is also preferred that the method allows a at least 1-year, 2-year, 3-year, 4-year, 5-year, 6-year, 7-year, 8-year, 9-year, or 10-year survival prognosis (after diagnosis)/a survival prognosis of at least up to about 1 year, 2 years, 3 years, 4 years, 5 years, 6 years, 7 years, 8 years, 9 years, or 10 years (after diagnosis).

The prognostic method can be used clinically to determine the survival prognosis/survival probability of an individual suffering from HNSCC. In particular, the method of providing a survival prognosis to an individual suffering from HNSCC is a valuable tool in predicting whether overall (or long-term) survival of the individual, e.g. following therapy, is likely. The prognostic method can also be used clinically to make treatment decisions by choosing the most appropriate treatment modalities for any particular individual suffering from HNSCC. In particular, the method of providing a survival prognosis to an individual suffering from HNSCC is a valuable tool in predicting if an individual is likely to respond favorably to a treatment regimen, such as drug therapy, chemotherapy, radiotherapy, and/or surgical intervention.

In one embodiment, the level of the at least one eIF is compared to a reference level of said at least one eIF.

The above comparison allows to determine the survival prognosis/probability of the individual suffering from HNSCC.

The reference level may be any level which allows to determine the survival prognosis/probability of the individual suffering from HNSCC. It may be obtained from a (control) subject (i.e. a subject different from the individual to be tested) or from the same individual. In the latter case, the survival prognosis/probability of the individual suffering from HNSCC may be retested, e.g. in the form of a longitudinal monitoring. It may be determined that the individual has now (in the re-test) a good survival prognosis/high survival probability and not a poor survival prognosis/low survival probability anymore or that the individual has now a poor survival prognosis/low survival probability (in the re-test) and not a good survival prognosis/high survival probability anymore. The re-test may be carried out regularly, e.g. every year or two times per year.

The reference level is preferably determined at the time of HNSCC diagnosis, immediately after HNSCC diagnosis, e.g. within 1 week, 2 weeks, 3 weeks, or 1 month after HNSCC diagnosis, or within a time period after HNSCC diagnosis, e.g. within a time period of no more than 1 week, 2 weeks, 3 weeks, or 1 month after HNSCC diagnosis of the (control) subject. Preferably, the level and the reference level are determined at the same time points, e.g. at the time of HNSCC diagnosis, or during the same time period.

The reference level may be the level determined by measuring at least one reference biological sample from at least one healthy subject and/or at least one subject suffering from HNSCC.

Preferably, the reference level is the level determined by measuring at least one reference biological sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference biological sample(s), from at least one subject suffering from HNSCC, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 subject(s) suffering from HNSCC.

More preferably,
the level of the at least one eIF comparable with or above the reference level indicates that the individual has a poor survival prognosis, or
the level of the at least one eIF below the reference level indicates that the individual has a good survival prognosis.

Even more preferably, the level of the at least one eIF is at least 0.6-fold or 0.7-fold, more preferably at least 0.8-fold or 0.9-fold, even more preferably at least 1.2-fold or 1.5-fold, and most preferably at least 2.0-fold or 3.0-fold above/below the reference level. For example, the level of the at least one eIF is at least 0.6-fold, at least 0.7-fold, at least 0.8-fold, at least 0.9-fold, at least 1.0-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, or at least 3.0-fold above/below the reference level.

A level which is comparable with the reference level is preferably identical with the reference level.

In one another (additional or alternative) embodiment, the level of the at least one eIF kinase is compared to a reference level of said at least one eIF kinase.

The above comparison allows to determine the survival prognosis/probability of the individual suffering from HNSCC.

The reference level may be any level which allows to determine the survival prognosis/probability of the individual suffering from HNSCC. It may be obtained from a (control) subject (i.e. a subject different from the individual to be tested) or from the same individual. In the latter case, the survival prognosis/probability of the individual suffering from HNSCC may be retested, e.g. in the form of a longitudinal monitoring. It may be determined that the individual has now (in the re-test) a good survival prognosis/high survival probability and not a poor survival prognosis/low survival probability anymore or that the individual has now a poor survival prognosis/low survival probability (in the re-test) and not a good survival prognosis/high survival probability anymore. The re-test may be carried out regularly, e.g. every year or two times per year.

The reference level is preferably determined at the time of HNSCC diagnosis, immediately after HNSCC diagnosis, e.g. within 1 week, 2 weeks, 3 weeks, or 1 month after HNSCC diagnosis, or within a time period after HNSCC diagnosis, e.g. within a time period of no more than 1 week, 2 weeks, 3 weeks, or 1 month after HNSCC diagnosis of the (control) subject. Preferably, the level and the reference level are determined at the same time points, e.g. at the time of HNSCC diagnosis, or during the same time period.

The reference level may be the level determined by measuring at least one reference biological sample from at least one healthy subject and/or at least one subject suffering from HNSCC.

Preferably, the reference level is the level determined by measuring at least one reference biological sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference biological sample(s), from at least one subject suffering from HNSCC, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 subject(s) suffering from HNSCC.

More preferably,
the level of the at least one eIF kinase comparable with or below the reference level indicates that the individual has a poor survival prognosis, or
the level of the at least one eIF kinase above the reference level indicates that the individual has a good survival prognosis.

Even more preferably, the level of the at least one eIF kinase is at least 0.6-fold or 0.7-fold, more preferably at least 0.8-fold or 0.9-fold, even more preferably at least 1.2-fold or 1.5-fold, and most preferably at least 2.0-fold or 3.0-fold below/above the reference level. For example, the level of the at least one eIF kinase is at least 0.6-fold, at least 0.7-fold, at least 0.8-fold, at least 0.9-fold, at least 1.0-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, or at least 3.0-fold below/above the reference level.

A level which is comparable with the reference level is preferably identical with the reference level.

In the methods of the first and second aspect of the present invention, it is preferred that the biological sample is a tissue sample, e.g. tumor tissue sample, or a body fluid sample. It is also preferred that the reference biological sample is a tissue sample, e.g. tumor tissue sample, or a body fluid sample. Preferably, the body fluid sample is selected from the group consisting of a blood sample, an urine sample, a lymph sample, a saliva sample and a combination thereof. More preferably, the blood sample is a whole blood sample or a blood fraction sample. Even more preferably, the blood fraction sample is a blood serum sample or a blood plasma sample.

Preferably, the aforementioned samples are pre-treated before they are used in the methods of the first and second aspect of the present invention. Said pre-treatment may include treatments required to separate the at least one eIF and/or eIF kinase described herein, or to remove excessive material or waste. Furthermore, pre-treatments may aim at sterilizing samples and/or removing contaminants such as undesired cells, bacteria or viruses. Suitable techniques comprise centrifugation, extraction, fractioning, ultrafiltration, protein precipitation followed by filtration and purification and/or enrichment of compounds. Moreover, other pre-treatments are carried out in order to provide the at least one eIF at least one eIF kinase described herein in a form or concentration suitable for analysis.

In one preferred embodiment of the methods of the first and second aspect of the present invention, the biological sample used to determine the level of the at least one eIF and/or eIF kinase is a tissue sample, e.g. tumor tissue sample (obtainable e.g. by biopsy) or a body fluid sample. The eIF and/or eIF kinase markers of the present invention can be found in the tissue affected with the tumor and in body fluids like blood and blood components (e.g. plasma or serum).

According to another preferred embodiment of the methods of the first and second aspect of the present invention, the level of the at least one eIF and/or eIF kinase is determined by measuring mRNA or protein levels. The levels of the eIFs and/or eIF kinases in the methods of the first and second aspect of the present invention can be determined either by measuring mRNA molecules encoding said eIFs and/or eIF kinases or the eIFs and/or eIF kinases as such in form of proteins. Methods to determine mRNA levels and protein levels in a sample are well known. mRNA expression levels are usually measured by polymerase chain reaction (PCR), in particular by reverse transcription quantitative polymerase chain reaction (RT-PCR and qPCR) or real-time PCR. RT-PCR is used to create a cDNA from the mRNA. The cDNA may be used in a qPCR assay to produce fluorescence as the DNA amplification process progresses. This fluorescence is proportional to the original mRNA amount in the samples. Other methods to be used include Northern blots, Fluorescence in situ hybridization (FISH), microarrays, and RT-PCR combined with capillary electrophoresis. Protein levels of eIFs and/or eIF kinases are preferably determined using immunoassays. Such methods are based on the binding of an antibody, a derivative or a fragment thereof to its corresponding target (i.e. eIF or eIF kinase). Polyclonal and monoclonal antibodies can be used in such methods. Derivatives or fragments of antibodies include Fab fragments, F(ab')$_2$ fragments, Fv fragments, single chain antibodies and single domain antibodies. Preferred immunoassays include Western blot, Immunohistochemistry, ELISA (enzyme-linked immunosorbent assay), radioimmunoassays, fluorescence resonance energy transfer (FRET) or time resolved-FRET (TR-FRET). Immunoassays detection is possible in lymphoma and HCC. It is particularly preferred to use antibodies and derivatives or fragments of antibodies which have been obtained from a non-human source. These antigen binding molecules can be of porcine, rabbit, murine, camel or rat origin. Of course, it is also possible to use antibodies and derivatives or fragments thereof which are recombinantly produced in plants or cell cultures, in particular microbial cell cultures (e.g. bacteria, yeast).

It is particularly preferred that HNSCC is selected from the group consisting of Neoplasm Clinical Primary Tumor Stage (T), Neoplasm Clinical Regional Lymph Node Stage (N), and Neoplasm Clinical Distant Metastasis Stage (M).

In a third aspect, the present invention relates to the use of at least one eukaryotic Initiation Factor (eIF), wherein the at least one eIF is selected from the group consisting of eIF2S1, eIF2S2, eIF2S3, eIF2B1, eIF2B2, eIF2B3, eIF2B4, and eIF2B5, and/or at least one eIF kinase, wherein the at least one eIF kinase is selected from the group consisting of eIF2AK1, eIF2AK2, eIF2AK3, and eIF2AK4, for diagnosing Head and Neck Squamous Cell Carcinoma (HNSCC) in an individual (suspected of having HNSCC) or for providing a survival prognosis to an individual suffering from HNSCC.

For example, at least 1, 2, 3, 4, 5, 6, 7, or 8 eIF(s) and/or at least 1, 2, 3, or 4 eIF kinase(s) is (are) used. Preferably, eIF2S1 and/or eIF2AK1 is (are) used.

It is particularly preferred that HNSCC is selected from the group consisting of Neoplasm Clinical Primary Tumor Stage (T), Neoplasm Clinical Regional Lymph Node Stage (N), and Neoplasm Clinical Distant Metastasis Stage (M).

For the above mentioned use, the level of the above mentioned eIFs and/or eF kinases is determined in a biological sample from an individual to be tested. It is preferred that the biological sample is a tissue sample, e.g. tumor tissue sample, or body fluid sample. Preferably, the body fluid sample is selected from the group consisting of a blood sample, a urine sample, and a combination thereof. More preferably, the blood sample is a whole blood sample or a blood fraction sample. Even more preferably, the blood fraction sample is a blood serum sample or a blood plasma sample.

As to further preferred embodiments, it is referred to the first and second aspect of the present invention.

In a fourth aspect, the present invention relates to (the use of) a kit for diagnosing Head and Neck Squamous Cell Carcinoma (HNSCC) in an individual (suspected of having HNSCC) or for providing a survival prognosis to an individual suffering from HNSCC, wherein said kit comprises means for determining the level of at least one eukaryotic Initiation Factor (eIF), wherein the at least one eIF is selected from the group consisting of eIF2S1, eIF2S2, eIF2S3, eIF2B1, eIF2B2, eIF2B3, eIF2B4, and eIF2B5, and/or the level of at least one eIF kinase, wherein the at least one eIF kinase is selected from the group consisting of eIF2AK1, eIF2AK2, eIF2AK3, and eIF2AK4, in a biological sample from an individual.

For example, the kit comprises means for determining the level of at least 1, 2, 3, 4, 5, 6, 7, or 8 eIF(s) and/or means for determining the level of at least 1, 2, 3, or 4 eIF kinase(s). Preferably, the means are for determining the level of eIF2S1 and/or the level of eIF2AK1.

It is particularly preferred that HNSCC is selected from the group consisting of Neoplasm Clinical Primary Tumor Stage (T), Neoplasm Clinical Regional Lymph Node Stage (N), and Neoplasm Clinical Distant Metastasis Stage (M).

Said means may be primers or primer pairs allowing the detecting of the above mentioned eIFs and/or eIF kinases on the RNA transcript, e.g. mRNA, level and/or antibodies, antibody derivatives or fragments of antibodies allowing the detection of the above mentioned eIFs and/or eIF kinases on the protein level.

In addition, said means encompass dipstrips or dipsticks, e.g. urine or blood dipstrips or dipsticks. Said means are tools used to determine changes in individual's urine or blood. A dipstrip or dipstick comprises different chemical pads or reagents which react (e.g. change color, in particular by applying an immune assay) when immersed in (e.g. blood or urine), and then removed from the biological sample (e.g. urine or blood sample). The result can be read after a few minutes, preferably after a few seconds.

It is preferred that the kit is useful for conducting the methods of the first and second aspect of the present invention.

It is further preferred that the kit comprises
(i) a container, and/or
(ii) a data carrier.

Said data carrier may be a non-electronical data carrier, e.g. a graphical data carrier such as an information leaflet, an information sheet, a bar code or an access code, or an electronical data carrier such as a floppy disk, a compact disk (CD), a digital versatile disk (DVD), a microchip or another semiconductor-based electronical data carrier. The access code may allow the access to a database, e.g. an internet database, a centralized, or a decentralized database. The access code may also allow access to an application software that causes a computer to perform tasks for computer users or a mobile app which is a software designed to run on smartphones and other mobile devices.

Said data carrier may further comprise a reference level of the at least one eIF referred to herein.

In case that the data carrier comprises an access code which allows the access to a database, said reference level is deposited in this database.

In addition, the data carrier may comprise information or instructions on how to carry out the methods of the first to third aspect of the present invention.

Said kit may also comprise materials desirable from a commercial and user standpoint including a buffer(s), a reagent(s) and/or a diluent(s) for determining the level mentioned above.

In a fifth aspect, the present invention relates to an eukaryotic initiation factor (eIF) modulating compound for use in the treatment of HNSCC, wherein the at least one eIF is selected from the group consisting of eIF2S1, eIF2S2, eIF2S3, eIF2B1, eIF2B2, eIF2B3, eIF2B4, and eIF2B5. Preferably, the eIF is eIF2S1.

In a preferred embodiment, the eIF modulating compound is an eIF inhibiting/binding molecule or an eIF molecule.

In a more preferred embodiment,
(i) the eIF inhibiting/binding molecule is selected from the group consisting of an anti-RNA, a small interfering RNA (siRNA), a short hairpin RNA (shRNA), a polypeptide or peptide, preferably comprising at least one eIF binding site, and an antibody or an antibody fragment thereof, preferably comprising at least one eIF binding site, or
(ii) the eIF molecule is a nucleic acid molecule encoding the eIF.

In a specific embodiment of the present invention, the eIF modulating compound is Salubrinal. In particular, the eIF blocking/inhibiting compound is Salubrinal. Salubrinal blocks/inhibits the eIFs, preferably eIF2S1. The present inventors found that Salubrinal acts by selectively inhibiting eIF2S1 phosphatase and, thus, blocks eIF2S1. The inhibition of eIF2S1 by Salubrinal in HNSCC has not been described yet.

It is particularly preferred that HNSCC is selected from the group consisting of Neoplasm Clinical Primary Tumor Stage (T), Neoplasm Clinical Regional Lymph Node Stage (N), and Neoplasm Clinical Distant Metastasis Stage (M).

It is also particularly preferred that the eIF modulating compound is suitable to be administered topically, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctivally, intravesicularly, mucosally, intrapericardially, intraumbilically, orally, by inhalation, by injection, by infusion, by continuous infusion, by localized perfusion bathing target cells directly, via a catheter, or via a lavage.

It is further particularly preferred that the eIF modulating compound is suitable to be administered by providing a delivery system selected from the group consisting of an expression construct, e.g. a vector, like a viral vector, such as an adenovirus, an adeno-associated virus, a retrovirus, or a lentivirus vector, a liposome, a polymer-mediated delivery system, a conjugate delivery system, an exosome, a microsponge, and a nanoparticle, e.g. a gold particle.

This aspect of the present invention can also be worded as follows: In a fifth aspect, the present invention relates to the use of an eukaryotic initiation factor (eIF) modulating compound for the manufacture of a medicament for the treatment of HNSCC, wherein the at least one eIF is selected from the group consisting of eIF2S1, eIF2S2, eIF2S3, eIF2B1, eIF2B2, eIF2B3, eIF2B4, and eIF2B5. Alternatively, the present invention relates in a fifth aspect to a method for treating HNSCC in an individual comprising the step of: administering (an effective amount of) an eIF modulating compound to an individual in need thereof, wherein the at least one eIF is selected from the group consisting of eIF2S1, eIF2S2, eIF2S3, eIF2B1, eIF2B2, eIF2B3, eIF2B4, and eIF2B5.

In a sixth aspect, the present invention relates to a combination of an eIF modulating compound and a drug different from an eIF modulating compound for use in the treatment of HNSCC, wherein the at least one eIF is selected from the group consisting of eIF2S1, eIF2S2, eIF2S3, eIF2B1, eIF2B2, eIF2B3, eIF2B4, and eIF2B5. Preferably, the eIF is eIF2S1.

In one preferred embodiment, the
(i) the eIF modulating compound is an eIF binding/inhibiting molecule or an eIF molecule, and/or
(ii) the drug different from a eIF modulating compound is selected from the group consisting of a drug used in cancer therapy, immunotherapy, chemotherapy, hormone therapy, gene therapy, and infectious therapy.

In one particular preferred embodiment, the
(i) the eIF modulating compound is an eIF binding/inhibiting molecule or an eIF molecule, and/or
(ii) the drug different from a eIF modulating compound is selected from the group consisting of a drug used in HNSCC cancer therapy, HNSCC immunotherapy, HNSCC chemotherapy, HNSCC hormone therapy, HNSCC gene therapy, and HNSCC infectious therapy.

In one more preferred embodiment,
(i) the eIF inhibiting/binding molecule is selected from the group consisting of an anti-RNA, a small interfering RNA (siRNA), a short hairpin RNA (shRNA), a polypeptide or peptide, preferably comprising at least one eIF binding site, and an antibody or an antibody fragment thereof, preferably comprising at least one eIF binding site, or
(ii) the eIF molecule is a nucleic acid molecule encoding the eIF.

In a specific embodiment of the present invention, the eIF modulating compound is Salubrinal. In particular, the eIF blocking/inhibiting compound is Salubrinal. Salubrinal blocks/inhibits the eIFs, preferably eIF2S1. The present inventors found that Salubrinal acts by selectively inhibiting eIF2S1 phosphatase and, thus, blocks eIF2S1. The inhibition of eIF2S1 by Salubrinal in HNSCC has not been described yet.

It is particularly preferred that HNSCC is selected from the group consisting of Neoplasm Clinical Primary Tumor Stage (T), Neoplasm Clinical Regional Lymph Node Stage (N), and Neoplasm Clinical Distant Metastasis Stage (M).

It is also particularly preferred that the combination is suitable to be administered topically, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctivally, intravesicularly, mucosally, intrapericardially, intraumbilically, orally, by inhalation, by injection, by infusion, by continuous infusion, by localized perfusion bathing target cells directly, via a catheter, or via a lavage.

It is also particularly preferred that the combination is suitable to be administered by providing a delivery system selected from the group consisting of an expression construct, e.g. a vector, like a viral vector, such as an adenovirus, an adeno-associated virus, a retrovirus, or a lentivirus vector, a liposome, a polymer-mediated delivery system, a conjugate delivery system, an exosome, a microsponge, and a nanoparticle, e.g. a gold particle.

The components of the combination, i.e. the eIF modulating compound and the drug different from a eIF modulating compound, may be administered together or independent from each other (e.g. one after the other).

This aspect of the present invention can also be worded as follows: In a sixth aspect, the present invention relates to a combination of an eIF modulating compound and a drug different from an eIF modulating compound for the manufacture of a medicament for the treatment of HNSCC, wherein the at least one eIF is selected from the group consisting of eIF2S1, eIF2S2, eIF2S3, eIF2B1, eIF2B2, eIF2B3, eIF2B4, and eIF2B5. Alternatively, the present invention relates in a sixth aspect to a method for treating HNSCC in an individual comprising the step of: administering (an effective amount of) a combination of an eIF modulating compound and a drug different from an eIF modulating compound, wherein the at least one eIF is selected from the group consisting of eIF2S1, eIF2S2, eIF2S3, eIF2B1, eIF2B2, eIF2B3, eIF2B4, and eIF2B5.

The components of the combination, i.e. the eIF modulating compound and the drug different from a eIF modulating compound, may be administered together or independent from each other (e.g. one after the other).

In an seventh aspect, the present invention relates to a pharmaceutical composition comprising the eIF modulating compound as defined in the fifth aspect of the present invention or the combination as defined in the sixth aspect of the present invention and a pharmaceutical acceptable carrier for use in the treatment of HNSCC.

It is particularly preferred that HNSCC is selected from the group consisting of Neoplasm Clinical Primary Tumor Stage (T), Neoplasm Clinical Regional Lymph Node Stage (N), and Neoplasm Clinical Distant Metastasis Stage (M).

The pharmaceutical composition may be formulated for local administration or systemic administration. In particular, the local administration is by parenteral administration, e.g. by intravenous administration, subcutaneous administration, intradermal administration, intramuscularly administration, and the systemic administration is by intraarterial administration.

In particular the composition is administered subcutaneously, intradermally, or intramuscularly.

The composition may further comprise one or more pharmaceutically acceptable carriers, diluents, and/or excipients.

The present invention is summarized as follows:
1. A method of diagnosing Head and Neck Squamous Cell Carcinoma (HNSCC) in an individual (suspected of having HNSCC) comprising the step of:
   determining the level of at least one eukaryotic Initiation Factor (eIF), wherein the at least one eIF is selected from the group consisting of eIF2S1, eIF2S2, eIF2S3, eIF2B1, eIF2B2, eIF2B3, eIF2B4, and eIF2B5, and/or the level of at least one eIF kinase, wherein the at least one eIF kinase is selected from the group consisting of eIF2AK1, eIF2AK2, eIF2AK3, and eIF2AK4, in a biological sample from an individual (suspected of having HNSCC).
2. The method of item 1, wherein the level of the at least one eIF is compared to a reference level of said at least one eIF.
3. The method of item 2, wherein the reference level is the level determined by measuring at least one reference biological sample from at least one healthy subject.
4. The method of items 2 or 3, wherein the level of the at least one eIF above the reference level indicates that the individual suffers from HNSCC.

5. The method of any one of items 1 to 4, wherein the level of the at least one eIF kinase is compared to a reference level of said at least one eIF kinase.
6. The method of item 5, wherein the reference level is the level determined by measuring at least one reference biological sample from at least one healthy subject.
7. The method of items 5 or 6, wherein the level of the at least one eIF kinase below the reference level indicates that the individual suffers from HNSCC.
8. A method of providing a survival prognosis to an individual suffering from Head and Neck Squamous Cell Carcinoma (HNSCC) comprising the step of:
   determining the level of at least one eukaryotic Initiation Factor (eIF), wherein the at least one eIF is selected from the group consisting of eIF2S1, eIF2S2, eIF2S3, eIF2B1, eIF2B2, eIF2B3, eIF2B4, and eIF2B5, and/or the level of at least one eIF kinase, wherein the at least one eIF kinase is selected from the group consisting of eIF2AK1, eIF2AK2, eIF2AK3, and eIF2AK4, in a biological sample from an individual (suspected of having HNSCC).
9. The method of item 8, wherein the level of the at least one eIF is compared to a reference level of said at least one eIF.
10. The method of item 9, wherein the reference level is the level determined by measuring at least one reference biological sample from at least one subject suffering from HNSCC.
11. The method of items 9 or 10, wherein
   the level of the at least one eIF comparable with or above the reference level indicates that the individual has a poor survival prognosis, or
   the level of the at least one eIF below the reference level indicates that the individual has a good survival prognosis.
12. The method of any one of items 8 to 11, wherein the level of the at least one eIF kinase is compared to a reference level of said at least one eIF kinase.
13. The method of item 12, wherein the reference level is the level determined by measuring at least one reference biological sample from at least one subject suffering from HNSCC.
14. The method of items 12 or 13, wherein
   the level of the at least one eIF kinase comparable with or below the reference level indicates that the individual has a poor survival prognosis, or
   the level of the at least one eIF kinase above the reference level indicates that the individual has a good survival prognosis.
15. The method of any one of items 1 to 14, wherein the biological sample is a tissue sample or a body fluid sample.
16. The method of item 15, wherein the body fluid sample is blood, lymph, or saliva.
17. The method of item 16, wherein the blood is whole blood or a blood fraction, preferably serum or plasma.
18. The method of any one of items 1 to 17, wherein the level of the at least one eIF is determined by measuring mRNA or protein levels.
19. The method of any one of items 1 to 18, wherein HNSCC is selected from the group consisting of Neoplasm Clinical Primary Tumor Stage (T), Neoplasm Clinical Regional Lymph Node Stage (N), and Neoplasm Clinical Distant Metastasis Stage (M).
20. Use of at least one eukaryotic Initiation Factor (eIF), wherein the at least one eIF is selected from the group consisting of eIF2S1, eIF2S2, eIF2S3, eIF2B1, eIF2B2, eIF2B3, eIF2B4, and eIF2B5, and/or at least one eIF kinase, wherein the at least one eIF kinase is selected from the group consisting of eIF2AK1, eIF2AK2, eIF2AK3, and eIF2AK4, for diagnosing Head and Neck Squamous Cell Carcinoma (HNSCC) in an individual (suspected of having HNSCC) or for providing a survival prognosis to an individual suffering from HNSCC.
21. The use of item 20, wherein HNSCC is selected from the group consisting of Neoplasm Clinical Primary Tumor Stage (T), Neoplasm Clinical Regional Lymph Node Stage (N), and Neoplasm Clinical Distant Metastasis Stage (M)
22. A kit for diagnosing Head and Neck Squamous Cell Carcinoma (HNSCC) in an individual (suspected of having HNSCC) or for providing a survival prognosis to an individual suffering from HNSCC, wherein said kit comprises
   means for determining the level of at least one eukaryotic Initiation Factor (eIF), wherein the at least one eIF is selected from the group consisting of eIF2S1, eIF2S2, eIF2S3, eIF2B1, eIF2B2, eIF2B3, eIF2B4, and eIF2B5, and/or the level of at least one eIF kinase, wherein the at least one eIF kinase is selected from the group consisting of eIF2AK1, eIF2AK2, eIF2AK3, and eIF2AK4, in a biological sample from an individual.
23. The kit of item 22, wherein HNSCC is selected from the group consisting of Neoplasm Clinical Primary Tumor Stage (T), Neoplasm Clinical Regional Lymph Node Stage (N), and Neoplasm Clinical Distant Metastasis Stage (M).
24. An eukaryotic initiation factor (eIF) modulating compound for use in the treatment of HNSCC, wherein the at least one eIF is selected from the group consisting of eIF2S1, eIF2S2, eIF2S3, eIF2B1, eIF2B2, eIF2B3, eIF2B4, and eIF2B5.
25. The eIF modulating compound for use of item 24, wherein the eIF modulating compound is an eIF binding/inhibiting molecule or an eIF molecule.
26. The eIF modulating compound for use of item 25, wherein
   (i) the eIF binding/inhibiting molecule is selected from the group consisting of an anti-RNA, a small interfering RNA (siRNA), a short hairpin RNA (shRNA), a polypeptide or peptide, and an antibody or an antibody fragment thereof, or
   (ii) the eIF molecule is a nucleic acid molecule encoding the eIF.
27. The eIF modulating compound for use of any one of items 24 to 26, wherein HNSCC is selected from the group consisting of Neoplasm Clinical Primary Tumor Stage (T), Neoplasm Clinical Regional Lymph Node Stage (N), and Neoplasm Clinical Distant Metastasis Stage (M).
28. A combination of an eIF modulating compound and a drug different from an eIF modulating compound for use in the treatment of HNSCC, wherein the at least one eIF is selected from the group consisting of eIF2S1, eIF2S2, eIF2S3, eIF2B1, eIF2B2, eIF2B3, eIF2B4, and eIF2B5.
29. The combination for use of item 28, wherein
   (i) the eIF modulating compound is an eIF binding/inhibiting molecule or an eIF molecule, and/or
   (ii) the drug different from a eIF modulating compound is selected from the group consisting of a drug used in cancer therapy, immunotherapy, chemotherapy, hormone therapy, gene therapy, and infectious therapy.

30. The combination for use of item 29, wherein
   (i) the eIF binding/inhibiting molecule is selected from the group consisting of an anti-RNA, a small interfering RNA (siRNA), a short hairpin RNA (shRNA), a polypeptide or peptide, and an antibody or an antibody fragment thereof, or
   (ii) the eIF molecule is a nucleic acid molecule encoding the eIF.
31. The combination for use of any one of items 28 to 30, wherein HNSCC is selected from the group consisting of Neoplasm Clinical Primary Tumor Stage (T), Neoplasm Clinical Regional Lymph Node Stage (N), and Neoplasm Clinical Distant Metastasis Stage (M).
32. A pharmaceutical composition comprising the eIF modulating compound as defined in any one of items 24 to 27 or the combination as defined in any one of items 28 to 31 and a pharmaceutical acceptable carrier for use in the treatment of HNSCC.
33. The pharmaceutical composition of item 32, wherein HNSCC is selected from the group consisting of Neoplasm Clinical Primary Tumor Stage (T), Neoplasm Clinical Regional Lymph Node Stage (N), and Neoplasm Clinical Distant Metastasis Stage (M).
34. A method for treating HNSCC in an individual comprising the step of:
   administering (an effective amount of) an eIF modulating compound to an individual in need thereof, wherein the at least one eIF is selected from the group consisting of eIF2S1, eIF2S2, eIF2S3, eIF2B1, eIF2B2, eIF2B3, eIF2B4, and eIF2B5.

Various modifications and variations of the invention will be apparent to those skilled in the art without departing from the scope of invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art in the relevant fields are intended to be covered by the present invention.

BRIEF DESCRIPTION OF THE FIGURES

The following Figures are merely illustrative of the present invention and should not be construed to limit the scope of the invention as indicated by the appended claims in any way.

EXAMPLES

Figures 1, 2:
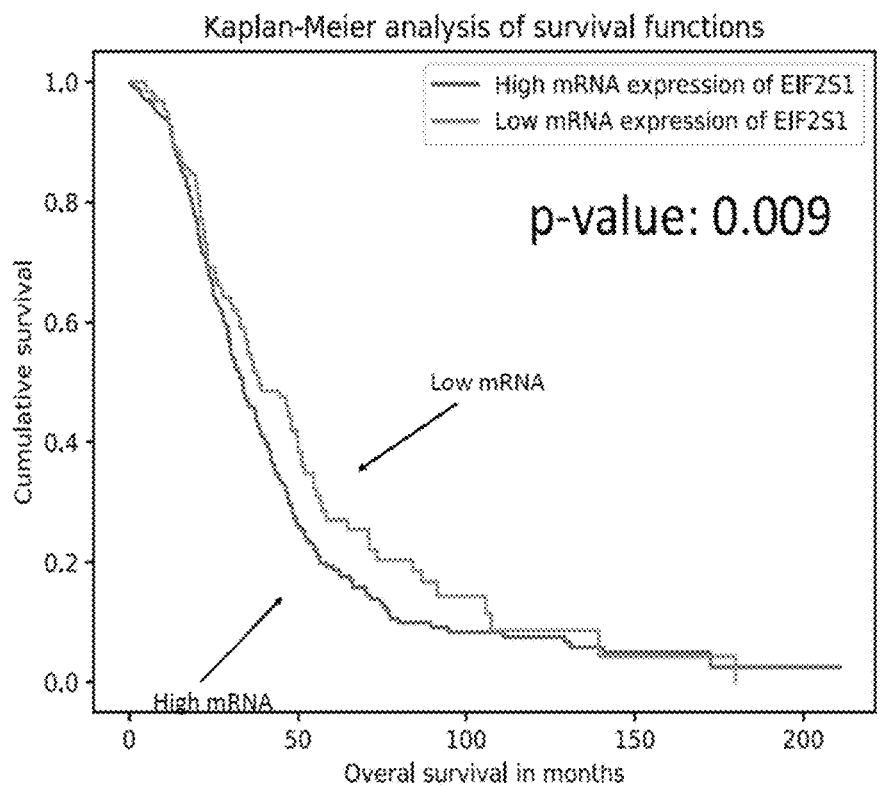
FIG. 1: Shows a Kaplan-Meier analysis of survival functions. High mRNA Expression of EIF2S1/eIF2α correlated with low survival prognosis. Light grey=low mRNA expression of EIF2S1/eIF2α, dark grey=high mRNA expression of EIF2S1/eIF2α.
FIG. 2: Shows that mRNA expression of EIF2S1/eIF2α is prognostic relevant (Spearman correlation rank)
Figure 3A:
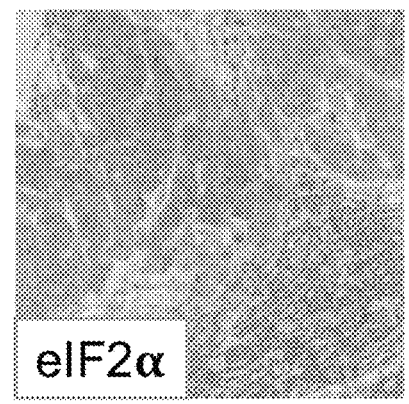
FIG. 3: Shows that EIF2S1/eIF2α is upregulated in HNSCC (3A immunostaining, 3B diagram with results of immunostaining).
Figure 3B:
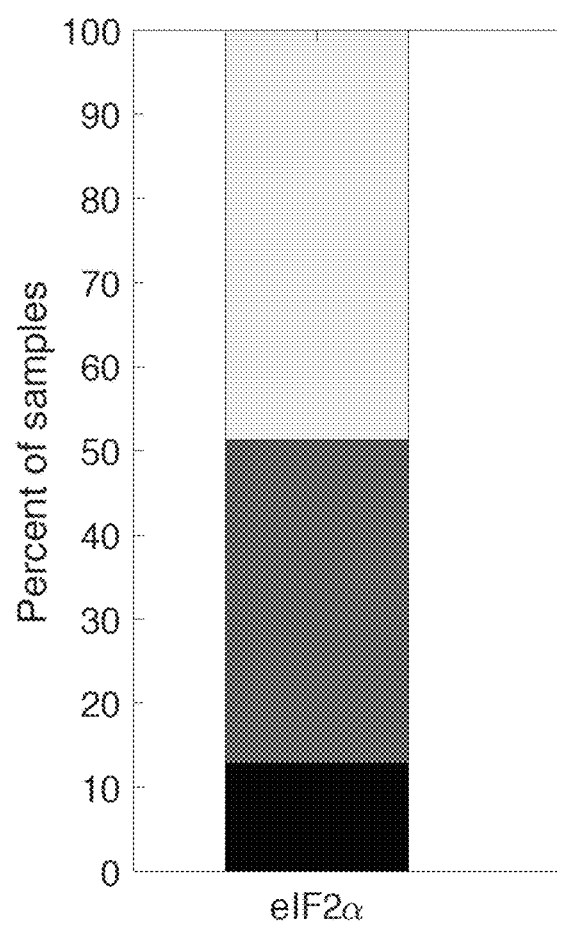
Figure 3B:
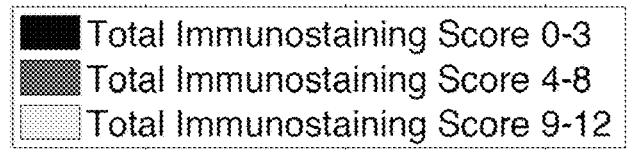
Figure 4:
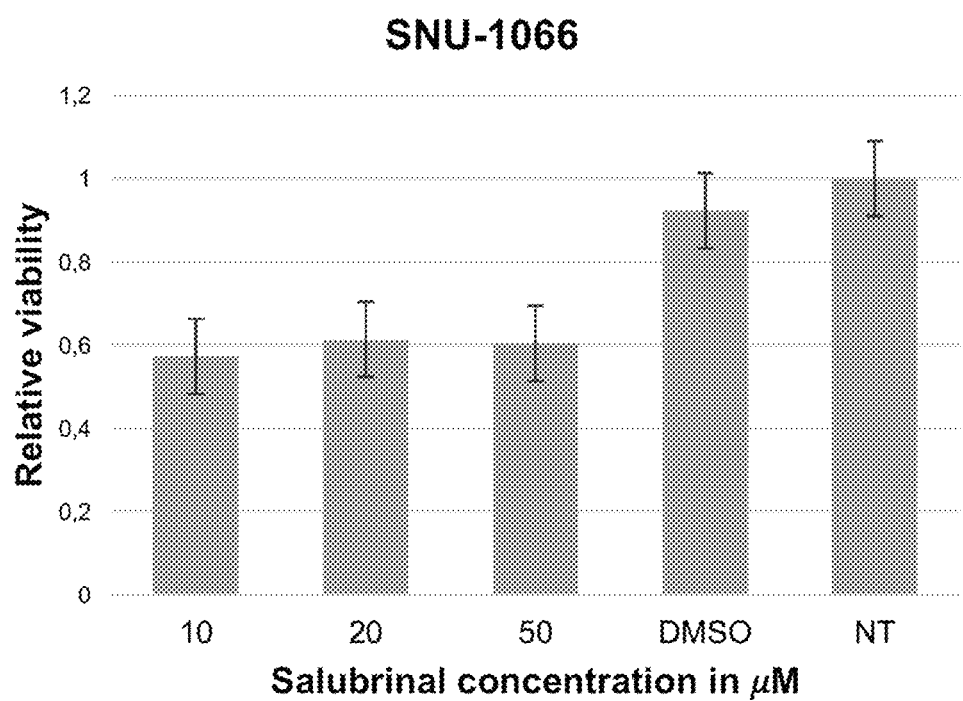
FIG. 4: Shows that treatment with EIF2S1/eIF2α inhibitor Salubrinal leads to a reduction in cell viability.
Figure 5:
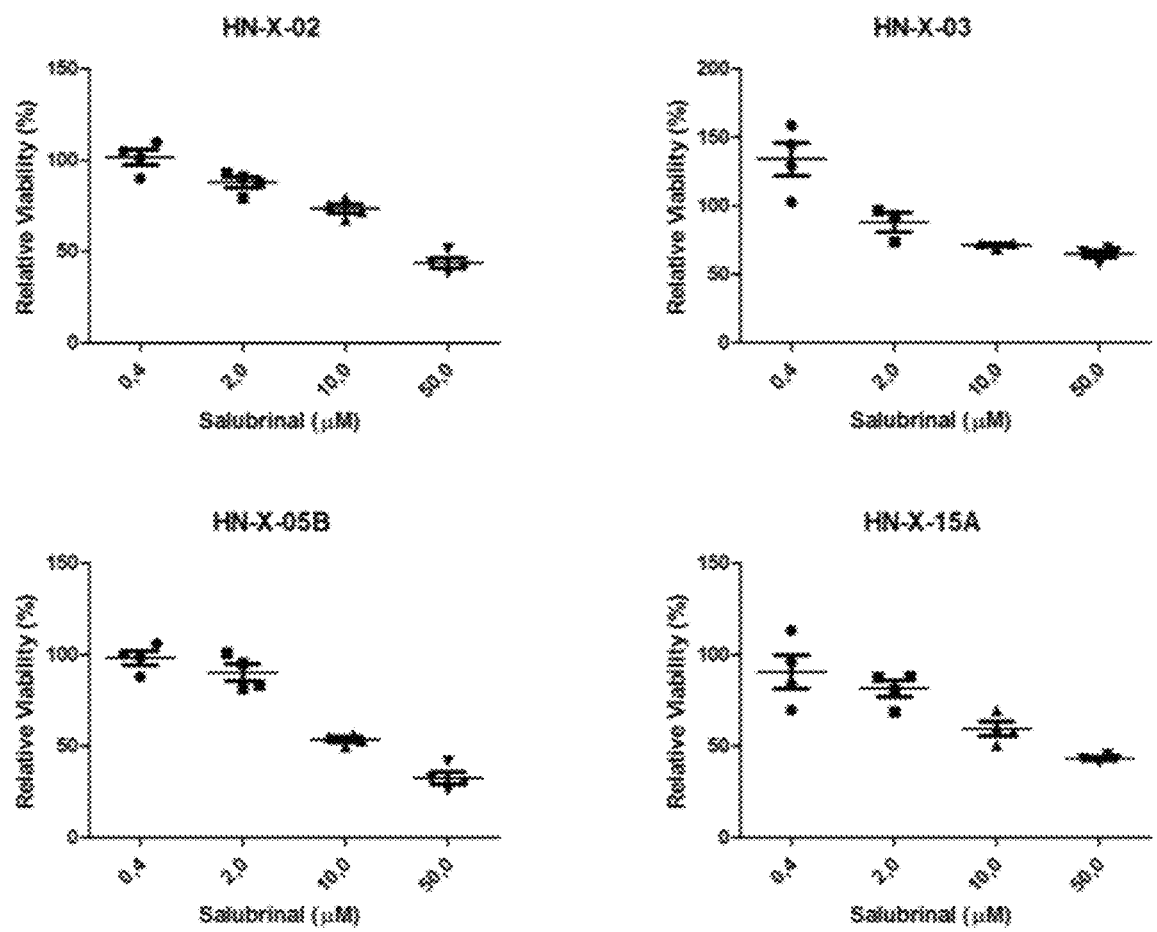
FIG. 5: Shows that EIF2S1/eIF2α inhibitor Salubrinal leads to reduction of cell viability in 3D-cell culture.

The examples given below are for illustrative purposes only and do not limit the invention described above in any way.

Methods
Bioinformatics

A multivariate analysis of the expression data of 279 HNSCC cases—data were available via cBioPortal.com—was performed. Patients were divided into two groups with high and low mRNA expression of the following genes: EIF2A, EIF2S1, EIF2S2, EIF2S3, EIF2AK1, EIF2AK2, EIF2AK3, EIF2AK4, EIF2B1, EIF2B2, EIF2B3, EIF2B4, EIF2B5. The overall survival of both groups was compared with the log-rank test. $p<0.05$ was considered to be significant.

Immunohistochemistry

Immunohistochemical tests were performed using an ultraView Universal DAB detection kit (Ventana Roche) on an automated immunostaining device (BenchMark Ultra, Roche}. From tissue fixed in formalin and embedded in paraffin thin sections of 4 µm were prepared, deparaffinated, rehydrated and subjected to a heat-induced antigen demasking. The cuts were then pre-conditioned according to the Manufacturer's instructions and wrapped with Canada Balsam.

The sections were then evaluated by two independently acting pathologists (S. S. and R. M.} by light microscopy. The intensity score was determined by comparison with the staining of a control: 0=no staining; 1=weak staining; 2=moderate staining; 3=strong staining. The proportional score corresponded to the percentage of stained tumor cells: 0% —O; <20% —1; 21-50% —2; 51-80%—3; >80%—4. The total immune-staining score was calculated by multiplying the two values. In total, 74 HNSCC samples were examined. The tumors were taken from the following sites: Larynx, hypopharynx, oropharynx, epipharynx, oral floor, palate, tonsilla, tongue and base of tongue. 24 samples of appropriate non-tumorous tissue were tested for comparison. The median values of IS, PS and TIS for normal tissue and the HNSCC samples were compared using the Kruskal-Willis test. The significance level was set at $p<0.05$.

MTT Assay in Cell Culture

Cell viability assays were carried out with 3 moderately differentiated laryngeal cancer cell lines (SNU-899, SNU-1066, SNU-1214}. MTT reagent stock solution was prepared by dissolving 5 mg crystal in 1 ml PBS and filter sterilization. The cell culture medium was aspirated and replaced by 100 µl fresh medium and 10 µl MTT stock solution per well. The plates were incubated at 37° C. for two hours. The supernatant was removed and 100 µl DMSO was added to each well. After 15-minute incubation at room temperature in a orbital shaker the absorption at 560 m was detected. All measurements were performed three times using GloMax@-Multi+Microplate Multimode Reader (Promega, Germany}. All experiments were performed three times with three repetitions.

Patient Derived 3D-Organoids (PD30} and Chemosensitivity Testing

Tumor samples from patients, who have undergone resection in the ENT clinic of Otto-von-Guericke University in Magdeburg, were incubated overnight in the RPM medium containing penicillin, streptomycin and amphotericin. On the following day, the tissue samples were crushed, passed through a sieve set to produce a size fraction of between 30 and 100 m, which were then incubated on 24-well plates at 37° C. The PD30s were incubated with Salubrinal in a 384-well culture plate for 72 h (i.e. the double population doubling time}. Thereafter, the CellTiter-Glo® luminescence cell viability assay was performed. The reagent mixture was assembled according to the manufacturer's instructions. All experiments were performed three times with three repetitions Results mRNA expression data of 279 HNSCC patients were analysed and for patients with strong/high expression of all subunits of eIF2 (i.e. EIF2S1, EIF2S2, EIF2S3, EIF2B1, EIF2B2, EIF2B3, EIF2B4, and/or EIF2B5) and low expression of the eIF2 kinases (i.e. EIF2AK1, EIF2AK2, EIF2AK3, and/or EIF2AK4) a lower overall survival was found. It was also found that all subunits of eIF2 (i.e. EIF2S1, EIF2S2, EIF2S3, EIF2B1, EIF2B2, EIF2B3, EIF2B4, and/or EIF2B5) were upregulated in HNSCC patients compared to healthy controls and that eIF2 kinases (i.e. EIF2AK1, EIF2AK2, EIF2AK3, and/or EIF2AK4) were downregulated in HNSCC patients compared to healthy controls. In particular, applying immunohistochemistry, an overexpression of EIF2S1 compared to non-tumorous tissue was shown. (p=0.039). Then, the effect of Salubrinal on the cell viability of cancer cells of the moderately differentiated SCC of the larynx was investigated. Incubating the cell culture with the active ingredient a 20-40% reduction of the viability of the cells was found, whereby the effect was dependent on the cell line. This effect was dependent on the dosage and the highest efficacy was observed at a dosage of 50 µM after 72 hours. Similarly, treating 3D-organoids of HNSCC derived from patient populations with the active substance a dose-dependent reduction of cell viability (average IC50 of 56 µM (in the range of between 16-158 M) was found in almost all samples.

Thus, all subunits of eIF2 (i.e. EIF2S, EIF2S2, EIF2S3, EIF2B1, EIF2B2, EIF2B3, EIF2B4, and/or EIF2B5) and eIF2 kinases (i.e. EIF2AK1, EIF2AK2, EIF2AK3, and/or EIF2AK4) are useful diagnostic markers as well as a therapeutic targets for HNSCC.

The invention claimed is:

1. A method of diagnosing and treating Head and Neck Squamous Cell Carcinoma (HNSCC) in an individual comprising the step of:
   (ia) determining the level of at least one eukaryotic Initiation Factor (eIF) in a head or neck tissue sample from the individual, wherein the at least one eIF is selected from the group consisting of eIF2S1, eIF2S2, eIF2S3, eIF2B1, eIF2B2, eIF2B3, eIF2B4, and eIF2B5,
   (iia) comparing the level of the at least one eIF to a reference level of the at least one eIF, wherein the reference level is the level determined by measuring at least one reference biological sample from at least one healthy subject,
   (iiia) diagnosing the individual as suffering from HNSCC when level of the at least one eIF is above the reference level, and
   (iva) administering to the individual diagnosed in step (iiia) as suffering from HNSCC anti-cancer drug therapy, immunotherapy, hormone therapy, gene therapy, infectious therapy, surgery, chemotherapy, or radiotherapy;

and/or
   (ib) determining the level of at least one eIF kinase in a head or neck tissue sample from the individual, wherein the at least one eIF kinase is selected from the group consisting of eIF2AK1, eIF2AK2, eIF2AK3, and eIF2AK4,
   (iib) comparing the level of the at least one eIF kinase to a reference level of said at least one eIF kinase, wherein the reference level is the level determined by measuring at least one reference biological sample from at least one healthy subject, and
   (iiib) diagnosing the individual as suffering from HNSCC when level of the at least one eIF kinase is below the reference level, and
   (ivb) administering to the individual diagnosed in step (iiib) as suffering from HNSCC anti-cancer drug therapy, immunotherapy, hormone therapy, gene therapy, infectious therapy, surgery, chemotherapy, or radiotherapy.

2. The method of claim 1, wherein the tissue sample is a sample taken from larynx, hypopharynx, oropharynx, epipharynx, oral floor, palate, tonsilla, tongue, or base of tongue.

3. The method of claim 1, wherein the level of the at least one eIF or eIF kinase is determined by measuring mRNA or protein level.

4. The method of claim 1, wherein the HNSCC is Neoplasm Clinical Primary Tumor Stage (T), Neoplasm Clinical Regional Lymph Node Stage (N), or Neoplasm Clinical Distant Metastasis Stage (M).

5. The method of claim 4, wherein the level of the at least one eIF is determined by measuring mRNA or protein levels.

6. The method of claim 4, wherein HNSCC is selected from the group consisting of Neoplasm Clinical Primary Tumor Stage (T), Neoplasm Clinical Regional Lymph Node Stage (N), and Neoplasm Clinical Distant Metastasis Stage (M).

7. The method of claim 4, wherein step (iva) or (ivb) comprises administering surgery, chemotherapy, and/or radiotherapy.

* * * * *